(12) United States Patent
Hari

(10) Patent No.: US 11,723,881 B2
(45) Date of Patent: *Aug. 15, 2023

(54) FORTIFIED CBD OIL FOR TREATMENT OF PTSD

(71) Applicant: Bright Green Corporation, Wilmington, DE (US)

(72) Inventor: V. Hari, Orlando, FL (US)

(73) Assignee: Bright Green Corporation, Wilmington, DE (US)

( * ) Notice: Subject to any disclaimer, the term of this patent is extended or adjusted under 35 U.S.C. 154(b) by 85 days.

This patent is subject to a terminal disclaimer.

(21) Appl. No.: 17/523,464

(22) Filed: Nov. 10, 2021

(65) Prior Publication Data

US 2022/0062198 A1  Mar. 3, 2022

Related U.S. Application Data

(62) Division of application No. 16/510,160, filed on Jul. 12, 2019, now Pat. No. 11,197,833.

(60) Provisional application No. 62/696,913, filed on Jul. 12, 2018.

(51) Int. Cl.
*A61K 31/05* (2006.01)
*A61K 9/14* (2006.01)
*A61K 9/107* (2006.01)
*A61K 31/12* (2006.01)
*A61K 9/00* (2006.01)
*A61K 36/185* (2006.01)

(52) U.S. Cl.
CPC ............ *A61K 31/05* (2013.01); *A61K 9/0053* (2013.01); *A61K 9/107* (2013.01); *A61K 9/148* (2013.01); *A61K 31/12* (2013.01); *A61K 36/185* (2013.01)

(58) Field of Classification Search
None
See application file for complete search history.

(56) References Cited

FOREIGN PATENT DOCUMENTS

CN    105288073    *   2/2016

* cited by examiner

*Primary Examiner* — Michael V Meller
(74) *Attorney, Agent, or Firm* — Carlson, Gaskey & Olds, P.C.

(57) ABSTRACT

A liquid capsule of *cannabis, ginseng*, and turmeric rhizome oil blend consisting essentially of an oil blend of *cannabis* oil, turmeric rhizome oil, and *ginseng* oil in a liquid capsule. There is less than 4 ppm of tetrahydrocannabinol (THC) in the oil blend.

4 Claims, No Drawings

FORTIFIED CBD OIL FOR TREATMENT OF PTSD

CROSS-REFERENCE TO RELATED APPLICATIONS

This application is a divisional of U.S. application Ser. No. 16/510,160 filed Jul. 12, 2019, which claims priority to U.S. Provisional Application No. 62/696,913, which was filed on Jul. 12, 2018, and is incorporated herein by reference.

BACKGROUND

This application relates to Cannabidiol (CBD) oil, and more particularly to a blended CBD oil for the treatment of stress-related health conditions, such as posttraumatic stress disorder (PTSD).

PTSD is a disorder that develops in some people who have experienced a shocking, scary, or dangerous event. Such events trigger many split-second changes in the body to help defend against danger or to avoid it. In many cases, people recover from initial symptoms after a few days or weeks. This is called acute stress disorder, or "ASD." Those who continue to experience the symptoms which last more than a month and seriously affect one's ability to function, and are not due to substance use, medical illness, or anything except the event itself, might be suffering from PTSD.

One can develop PTSD at any age. This includes war veterans, children, and people who have been through a physical or sexual assault, abuse, accident, disaster, climatic changes resulting in storms, hurricanes and other natural calamities, surgery, hospitalization, war, or many other serious events. The most prescribed medications for treating PTSD include antidepressants, sleep medications, and relaxants.

SUMMARY

An example blended oil composition includes a combination of Cannabidiol (CBD) oil extracted from *Cannabis sativa*, curcumin oil including one or more curcuminoids from turmeric rhizomes, and ginsenoside oil including one or more ginsenosides from at least one of *Panax ginseng* and *P. quinquefolius*, wherein the *Cannabis sativa* comprises at least one of *C. sativa, C. indica*, and *C. ruderalis*.

An example method of producing CBD oil includes extracting CBD oil from *Cannabis sativa*, wherein the *Cannabis sativa* comprises at least one of *C. sativa, C. indica*, and *C. ruderalis*; obtaining curcumin oil including one or more curcuminoids from turmeric rhizomes; obtaining ginsenoside oil from including one or more ginsenosides from at least one of *Panax ginseng* and *P. quinquefolius*; and blending the CBD, curcumin, and ginsenosides in a blended oil composition.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

DETAILED DESCRIPTION

The present disclosure describes a unique blend of *Cannabis* CBD oil, turmeric oil, and *ginseng* oil. In particular, the CBD oil is fortified with at least one curcuminoid from turmeric and at least one ginsenoside from *Panax ginseng* and/or *P. quinquefolius*. The blended CBD oil composition can be used for treating PTSD as well as other stress-related health conditions, for example. Each of these three ingredients are well-suited for treating PTSD and other stress related conditions since all three have anti-inflammatory, calming, and memory-enhancing properties, and as such, they are able to address the various manifestations of the syndrome.

In the unique formulations discussed herein, each of these three ingredients complements the pharmacology of the others, exhibiting a synergistic effect.

In one example, the blended oil composition includes less than 4 ppm of psychoactive tetrahydrocannabinol (THC). In a further example, the blended oil composition is free of THC.

The blended oil could be administered by prescription by authorized registered licensed physicians for treating PTSD and other stress related health conditions, for example.

The blended oil composition includes a combination of CBD, one or more curcuminoids (e.g., curcumin), and one or more ginsenosides. The CBD is obtained from extracts of *Cannabis sativa*, including at least one of *C. sativa, C. indica*, and *C. ruderalis* including its subspecies, varieties, strains, and biotypes. The CBD is fortified with the curcuminoid(s) from turmeric rhizomes, and ginsenoside(s) from at least one of *Panax ginseng* and *P. quinquefolius*. All three of the ingredients are combined to form a synergistic formulation.

The *Cannabis* plant extracts may be obtained from *C. sativa, C. indica* and *C. ruderalis* and/or any of their many sub species, strains, hybrids and biotypes grown in semi-automated, computerized greenhouses. Similarly, the Curcuminoids and ginsenosides from turmeric and ginseng can be purified from organically grown plants.

In the composition of some embodiments, the CBD oil contains a range of cannabinoids ranging from 2.5 mg-20 mg/ml and is fortified with not less than 250 mg/ml of Curcuminoids and 250 mg/ml of ginsenosides. Such fortified CBD oil can be incorporated into various beverages, tonics, liquid capsules, and tinctures. The amount may be varied to suit the needs of differing patients.

In one example, a liquid capsule for oral intake includes 1 ml of the fortified CBD oil. In one example, 1 ml of the fortified CBD oil is included in a 2 ounce dose of a liquid tonic.

One example composition is a beverage including 1 ml of the fortified CBD oil diluted with 8 ounces of liquid emulsion. The beverage in this example is fortified with a selected dosage, such as a minimum daily requirement of vitamins and minerals.

Although example embodiments have been disclosed, a worker of ordinary skill in this art would recognize that certain modifications would come within the scope of this disclosure. For that reason, the following claims should be studied to determine the scope and content of this disclosure.

What is claimed is:

1. A liquid capsule consisting essentially of *cannabis* oil, *ginseng* oil, and turmeric rhizome oil, wherein the oil blend is free of tetrahydrocannabinol.

2. The liquid capsule of claim 1, wherein the oil blend includes 2.5 mg/ml-20 mg/ml of *cannabis* oil, at least 250 mg/ml of rhizome oil, and at least 20 mg/ml of *ginseng* oil.

3. The liquid capsule of claim 1, wherein the rhizome oil and *ginseng* oil are organically grown.

4. The liquid capsule of claim 1, wherein the liquid capsule includes approximately 1 ml of the oil blend.

\* \* \* \* \*